United States Patent [19]

Attig et al.

[11] Patent Number: 4,827,001

[45] Date of Patent: May 2, 1989

[54] PREPARATION OF γ-BUTYROLACTONE AND 1,4-BUTANEDIOL BY CATALYTIC HYDROGENATION OF MALEIC ACID

[75] Inventors: Thomas G. Attig, Aurora; Anne M. Graham, Northfield, both of Ohio

[73] Assignee: The Standard Oil Company, Cleveland, Ohio

[21] Appl. No.: 115,945

[22] Filed: Nov. 2, 1987

[51] Int. Cl.$^4$ .................... C07D 307/32; C07C 31/18
[52] U.S. Cl. .................... 549/326; 568/864; 502/326
[58] Field of Search .................... 549/326; 568/864; 502/326

[56] References Cited

U.S. PATENT DOCUMENTS

| | | | |
|---|---|---|---|
| 4,089,810 | 5/1978 | Diwell et al. | 502/326 |
| 4,096,156 | 6/1978 | Freudenberger et al. | 549/326 |
| 4,297,245 | 10/1981 | Bartley et al. | 502/326 |
| 4,301,077 | 11/1981 | Pesa et al. | 549/508 |
| 4,398,039 | 8/1983 | Pesa et al. | 260/409 |

OTHER PUBLICATIONS

Stoop et al., "Formation of Olefins etc.", CA 105, No. 8952u., (1986).
Horner et al., "Ruthenium/Carbon—Hydrogenation, etc.", CA 99, No. 54020u, (1983).
Schay et al., "Catalytic Hydrogenation, etc.", CA 94, No. 29845f, (1981).
Knifton et al., "Catalytic Reduction of Aromatic, etc.", CA 77, No. 151655n, (1972).

Primary Examiner—Richard L. Raymond
Assistant Examiner—Susan P. Treanor
Attorney, Agent, or Firm—C. S. Lynch; D. J. Untener; L. W. Evans

[57] ABSTRACT

Disclosed is the hydrogenation of maleic acid in the presence of a solid iron-containing ruthenium catalyst containing the elements and the ratios indicated by the empirical formula, $$RuFe_aM_bO_x$$

where
M is one or more of Pd and Rh,
a is 0.1–5,
b is zero–3, and
x is a number sufficient to satisfy the valency requirements of the cations present in the catalyst, said process being effected by contacting in a reaction zone an excess of hydrogen with an aqueous solution of maleic acid in admixture with said catalyst.

5 Claims, No Drawings

PREPARATION OF γ-BUTYROLACTONE AND 1,4-BUTANEDIOL BY CATALYTIC HYDROGENATION OF MALEIC ACID

This invention relates to the preparation of γ-butyrolactone and 1,4-butanediol directly from maleic acid.

In the commercial preparation of maleic anydride, a relatively inexpensive stream comprising an aqueous solution of maleic acid is obtained in processing the reactor effluent.

It is an object of the present invention to provide a process useful for utilizing this relatively inexpensive starting material to make γ-butyrolactone or 1,4-butanediol.

Another more specific object is to provide a process for the liquid phase reaction of maleic acid with hydrogen to make such products.

Other objects, as well as aspects, features and advantages of the invention, will become apparent from a study of the specification including illustrative examples.

According to the present invention there is provided a process for making one or both of γ-butyrolactone and 1,4-butanediol by the hydrogenation of maleic acid in the presence of a solid iron-containing ruthenium catalyst containing the elements and the ratios indicated by the empirical formula,

$$RuFe_aM_bO_x$$

where
m is one or more of Pd and Rh,
a is 0.1–5.
b is zero –3, and
x is a number sufficient to satisfy the valency requirements of the cations present in the catalyst, said process being effected by contacting in a reaction zone an excess of hydrogen with an aqueous solution of maleic acid in admixture with said catalyst.

In the foregoing catalyst formula a is usually at least 2.25. Also, a is most often not over 2.

Ford U.S. Pat. No. 2,607,807 assigned to DuPont describes making alcohols by the hydrogenation of an unsubstituted mono or dicarboxylic acid in the presence of a ruthenium catalyst at pressures of at least 200, preferably 500, atmospheres hydrogen pressure. Water is not part of the charge. Ruthenium catalysts having iron are not mentioned. One example hydrogenates succinic acid to obtain tetramethylene glycol.

Gresham U.S. Pat. No. 2,607,805, also assigned to DuPont, describes the hydrogenation of hydrocarboxylic acids to polyhydroxy compounds using ruthenium catalysts, none of which contain iron.

Pesa and Graham U.S. Pat. No. 4,301,077 discloses inter alia the catalytic hydrogenation of maleic acid or anhydride using an oxide catalyst containing ruthenium, one or both of Ni and Pd, one or more of Fe, Co, Rh, Os, Ir and Pt, and one or both of Zn and Cd. The product can include 1,4-butanediol. In the process, the presence of water is to be avoided, but if water is present, the reaction is effected in the presence of less than 25 wt% water, based on the weight of the maleic acid or anhydride. On the other hand the present catalysts are used with aqueous feeds containing much larger amounts of water, usually containing a weight ratio of water to maleic acid of at least 2:3. Moreover, the present catalyst usually contains no Zn or Cd, but in any event the atomic ratio of the sum of Zn plus Cd to Ru is no more than 1:10,000.

In the present invention the pressure is well under 200 atmospheres, in fact not over 170 atmospheres, and usually no more than 2100 psi gage pressure. The hydrogen pressure is usually at least 40 atmospheres, more usually at least 1000 psi gage.

Pesa et al. U.S. Pat. No. 4,398,039 discloses the vapor phase hydrogenation of saturated monocarboxylic acids in the presence of ruthenium catalysts promoted with cobalt and/or nickel and possibly containing iron.

In the present process the usual reaction temperature is in the range from 120°–300° C., more often 175°–275° C. The substrate maleic acid can be introduced to the reaction zone as maleic anhydride where it hydrolyzes to the acid on reaction with the aqueous solvent.

In the present process the catalyst composition can be reduced by the hydrogen in the reaction zone. The catalyst can also be reduced, usually with hydrogen, prior to its initial contact with the substrate maleic acid, within the reaction zone or before being placed in the reactor.

The presence of the iron component of the present catalyst promotes greater selectivity and yield of the desired products in the presence of water. This makes it attractive to use the intermediate aqueous maleic acid solution of a maleic anhydride plant as the feed to a reactor for the liquid phase hydrogenation to either or both of γ-butyrolactone and 1,4-butanediol.

It will be understood that in the liquid phase hydrogenation reaction zone of the present process, most of the hydrogen is present in the gas phase.

The following examples illustrate the process of the invention but are not to be considered in any way limiting. All of the process examples were effected in the liquid phase aqueous solution, although most of the hydrogen remained in the gas phase, as will be understood.

EXAMPLE 1

150 cc of 10/30 mesh alumina was dried four hours at 125° C. A solution was made as follows: 9.12g of Fe(NO$_3$)$_3$.9H$_2$O and 6.54g of Ni(NO$_3$)$_2$.6H$_2$O were added to 56.88g of Ru(NO$_3$)$_3$ which had bee total of 75g with water. The alumina was impregnated with this solution using the incipient wetness technique. The application of the Fe-Ni-Ru was done in three steps, with drying after addition of each portion of the solution. After the third wetting or impregnation, the catalyst composition was dried overnight at 125° C. and then calcined for 3 hours at 350° C. Before using a portion of the catalyst in any run, it was reduced by contact with flowing H$_2$ gas overnight at 250° C.

EXAMPLE 2

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of H$_2$ at 250° C. for 15 hours. Then a 30 weight percent solution of maleic acid in water was fed by high pressure syringe pump into the top of the preheat zone, together with hydrogen gas. The molar ratio of H$_2$ to maleic acid was 24, the temperature was 250° C., the pressure was 1300 psig, and the contact time was 0.3 minutes. After about 5 hours pre-run, the product was passed through a room temperature condenser and the collected liquid was analyzed by gas chromatography. Conversion was 100 percent and the yield of γ-butyrolactone was 54.0%; the yield of 1,4-butanediol was 0.2%, based on the maleic acid fed.

EXAMPLE 3

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 24, the temperature was 250° C., the pressure was 1300 psig, and the contact time was 1.2 minutes. After about 5 hours pre-run, the product was passed through a room temperature condenser and the collected liquid was analyzed by gas chromatography. Conversion was 100 percent and the yield of γ-butyrolactone was 69.1%; the yield of 1,4-butanediol was 2.8%, based on the maleic acid fed.

EXAMPLE 4

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 24, the temperature was 250° C., the pressure was 1300 psig, and the contact time was 1.2 minutes. After about 5 hours pre-run, the product was passed through a room temperature condenser and the collected liquid was analyzed by gas chromatography. Conversion was 100 percent and the yield of γ-butyrolactone was 71.8%; the yield of 1,4-butanediol was 1.1%, based on the maleic acid fed.

EXAMPLE 5

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 24, the temperature was 250° C., the pressure was 1300 psig, and the contact time was 1.2 minutes. After about 5 hours pre-run, the product was passed through a room temperature condenser and the collected liquid was analyzed by gas chromatography. Conversion was 100 percent and the yield of γ-butyrolactone was 75.0%; the yield of 1,4-butanediol was 1.7%, based on the maleic acid fed.

EXAMPLE 6

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 24, the temperature was 250° C., the pressure was 1300 psig, and the contact time was 2.5 minutes. After about 5 hours pre-run, the product was passed through a room temperature condenser and the collected liquid was analyzed by gas chromatography. Conversion was 100 percent and the yield of γ-butyrolactone was 59.8%; the yield of 1,4-butanediol was 5.8%, based on the maleic acid fed.

EXAMPLE 7

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 32, the temperature was 250° C., the pressure was 1300 psig, and the contact time was 1.4 minutes. After about 5 hours pre-run, the product was passed through a room temperature condenser and the collected liquid was analyzed by gas chromatography. Conversion was 100 percent and the yield of γ-butyrolactone was 79.8%; the yield of 1,4-butanediol was 2.9%, based on the maleic acid fed.

EXAMPLE 8

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 12, the temperature was 250° C., the pressure was 1300 psig, and the contact time was 2.0 minutes. After about 5 hours pre-run, the product was passed through a room temperature condenser and the collected liquid was analyzed by gas chromatography. Conversion was 100 percent and the yield of γ-butyrolactone was 52.7%; the yield of 1,4-butanediol was 2.5%, based on the maleic acid fed.

EXAMPLE 9

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 48, the temperature was 250° C., the pressure was 1300 psig, and the contact time was 0.4 minutes. After about 5 hours pre-run, the product was passed through a room temperature condenser and the collected liquid was analyzed by gas chromatography. Conversion was 100 percent and the yield of γ-butyrolactone was 45.8%; the yield of 1,4-butanediol was 0.1%, based on the maleic acid fed. Note that the contact time was probably less than optimum.

EXAMPLE 10

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 48, the temperature was 250° C., the pressure was 1300 psig, and the contact time was 1.5 minutes. After about 5 hours pre-run, the product was passed through a room temperature condenser and the collected liquid was analyzed by gas chromatography. Conversion was 100 percent and the yield of γ-butyrolactone was 49.6%; the yield of 1,4-butanediol was 22.5%, based on the maleic acid fed.

EXAMPLE 11

A portion of the catalyst of Example 1 was placed in a high pressure tubular fixed bed reactor, and on top thereof was placed a zone of inert glass beads comprising a preheat zone. All flows were downward through the tubular reactor, which was externally heated to the reaction temperature. The catalyst was reduced in a stream of $H_2$ at 250° C. for 15 hours. Then a 30 weight percent solution of maleic acid in water was fed by high pressure syringe pump into the top of the preheat zone, together with hydrogen gas. The molar ratio of $H_2$ to maleic acid was 48, the temperature was 250° C., the pressure was 1300 psig, and the contact time was 1.9 minutes. After about 5 hours pre-run, the product was passed through a room temperature condenser and the collected liquid was analyzed by gas chromatography. Conversion was 100 percent and the yield of γ-butyrolactone was 63.7%; the yield of 1,4-butanediol was 1.2%, based on the maleic acid fed.

EXAMPLE 12

To 12.63g of an 8 percent aqueous ruthenium nitrate solution was added 1.05g $Fe(NO_3)_3.6H_2O$, followed by dilution to 25 ml with distilled water. This solution was stirred and heated and 25 ml of conc. ammonium hydroxide was added dropwise. The resulting slurry was slowly evaporated to dryness with periodic additions (1 ml) of ammonium hydroxide. The residue was then dried at 110° C. It was then heated according to the following schedule:

Heated to 125° C. at 1° C./min.
Held at 125° C. for 1 hour
Heated to 250° C. at 1° C./min.
Held at 250° C. for 1 hour
Heated to 350° C. at 1° C./min.
Held at 350° C. for 3 hours.

The empirical formula of the catalyst was $RuFe_{0.3}O_x$. It was ground to pass through a 140 mesh screen.

EXAMPLE 13

To 12.63g of an 8 percent aqueous ruthenium nitrate solution was added 1.40g $Fe(NO_3)_3.6H_2O$, followed by dilution to 25 ml with distilled water. This solution was stirred and heated and 25 ml of conc. ammonium hydroxide was added dropwise. The resulting slurry was slowly evaporated to dryness with periodic additions (1 ml) of ammonium hydroxide. The residue was then dried at 110° C. It was then heated according to the following schedule:

Heated to 125° C. at 1° C./min.
Held at 125° C. for 1 hour
Heated to 250° C. at 1° C./min.
Held at 250° C. for 1 hour
Heated to 350° C. at 1° C./min.
Held at 350° C. for 3 hours The empirical formula of the catalyst was $RuFe_{0.4}O_x$. It was ground to pass through a 140 mesh screen.

EXAMPLE 14

To 12.63g of an 8 percent aqueous ruthenium nitrate solution was added 1.75g $Fe(NO_3)_3.6H_2O$, followed by dilution to 25 ml with distilled water. This solution was stirred and heated and 25 ml of conc. ammonium hydroxide was added dropwise. The resulting slurry was slowly evaporated to dryness with perodic additions (1 ml) of ammonium hydroxide. The residue was then dried at 110° C. It was then heated according to the following schedule:

Heated to 125° C. at 1° C./min.
Held at 125° C. for 1 hour
Heated to 250° C. at 1° C./min.
Held at 250° C. for 1 hour
Heated to 350° C. at 1° C./min.
Held at 350° C. for 3 hours.

The empirical formula of the catalyst was $RuFe_{0.5}O_x$. It was ground to pass through a 140 mesh screen.

EXAMPLE 15

To 37.89g of an 8 percent aqueous ruthenium nitrate solution was added 3.15g $Fe(NO_3)_3.6H_2O$, followed by 25 ml of distilled water. This solution was stirred and heated and 25 ml of conc. ammonium hydroxide was added dropwise. The resulting slurry was slowly evaporated to dryness with periodic additions (1 ml) of ammonium hydroxide. The residue was then dried overnight at 110° C. It was then heated according to the following schedule:

Heated to 125° C. at 1° C./min.
Held at 125° C. for 1 hour
Heated to 250° C. at 1° C./min.
Held at 250° C. for 1 hour
Heated to 350° C. at 1° C./min.
Held at 350° C. for 3 hours.

The empirical formula of the catalyst was $RuFe_{0.3}O_x$. It was ground to pass through a 140 mesh screen.

EXAMPLE 16

To 12.63g of an 8 percent aqueous ruthenium nitrate solution was diluted to 25 ml with distilled water. This solution was stirred and heated and 25 ml of conc. ammonium hydroxide was added dropwise. The resulting slurry was slowly evaporated to dryness with periodic additions (1 ml) of ammonium hydroxide. The residue was then dried at 110° C. It was then heated according to the following schedule:

Heated to 125° C. at 1° C./min.
Held at 125° C. for 1 hour
Heated to 250° C. at 1° C./min.
Held at 250° C. for 1 hour
Heated to 350° C. at 1° C./min.
Held at 350° C. for 3 hours.

The empirical formula of the catalyst was $RuO_x$. It was ground to pass through a 140 mesh screen.

EXAMPLE 17

To 12.63g of an 8 percent aqueous ruthenium nitrate solution was added 1.05g $Co(NO_3)_3.6H_2O$ and the resulting solution was diluted to 25 ml with distilled water. This solution was stirred and heated and 25 ml of conc. ammonium hydroxide was added dropwise. The resulting slurry was slowly evaporated to dryness with periodic additions (1 ml) of ammonium hydroxide. The residue was then dried at 110° C. It was then heated according to the following schedule:

Heated to 125° C. at 1° C./min.
Held at 125° C. for 1 hour
Heated to 250° C. at 1° C./min.
Held at 250° C. for 1 hour
Heated to 350° C. at 1° C./min.
Held at 350° C. for 3 hours.

The empirical formula of the catalyst was $RuCo_{0.3}O_x$. It was ground to pass through a 140 mesh screen.

EXAMPLE 18

To 12.63g of an 8 percent aqueous ruthenium nitrate solution was added 2.91g $Ni(NO_3)_2.6H_2O$, followed by dilution to 50 ml with distilled water. This solution was stirred and heated and 25 ml of conc. ammonium hydroxide was added dropwise until the pH reached 9. The resulting dispersion was slowly evaporated to dryness on a hotplate with periodic additions (1 ml) of ammonium hydroxide. It was then heated according to the following schedule:

Heated to 125° C. at 1° C./min.
Held at 125° C. for 1 hour
Heated to 250° C. at 1° C./min.
Held at 250° C. for 2 hours
Heated to 350° C. at 1° C./min.
Held at 350° C. for 3 hours.

The empirical formula of the catalyst was $RuNiO_x$. It was ground to pass through a 140 mesh screen.

EXAMPLE 19

0.5g of the catalyst of Example 12, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 175 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 6.3% and 50.9%, respectively.

COMPARATIVE EXAMPLE A 0.5g of the catalyst of Example 18, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 175 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 18.8% and 0.5% respectively.

COMPARATIVE EXAMPLE B 0.5g of the catalyst of Example 17, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 170 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 30.9% and 2.7%, respectively.

COMPARATIVE EXAMPLE C 0.5g of the catalyst of Example 16, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was addd when the pressure dropped 50 to 100 psi to bring the pressure back to or near the original pressure at reaction temperature. The reaction was effected for 170 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 6.8% and 1.4%, respectively.

EXAMPLE 20

0.5g of the catalyst of Example 15, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 60 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 46.6% and 11.8%, respectively.

EXAMPLE 21

0.5g of the catalyst of Example 15, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 115 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 37.4% and 24.2%, respectively.

EXAMPLE 22

0.5g of the catalyst of Example 15, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1500 psig. As the reaction proceeded, additional hydrogen was added when the pressure dropped 50 to 100 psi to bring the pressure back to or near the original pressure at reaction temperature. The reaction was effected for 190 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 2.7% and 30.1%, respectively.

EXAMPLE 23

0.5g of the catalyst of Example 15, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 160° C. and the pressure adjusted to 1850 psig. As the reaction proceeded, additional hydrogen was added when the pressure dropped 50 to 100 psi to bring the pressure back to or near the original pressure at reaction temperature. The reaction was effected for 170 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 31.0% and 38.0%, respectively.

EXAMPLE 24

0.5g of the catalyst of Example 15, and then 50g of a 30 weight percent solution of maleic acid in water, were placed in the glass liner of a 300 ml autoclave, which was then sealed, purged several times with hydrogen and then pressurized with hydrogen to 1100 psig. The autoclave was heated to 160° C. and the pressure adjusted to 1850 psig. As the reaction proceeded, additional hydrogen was added when the pressure dropped 50 to 100 psi to bring the pressure back to or near the original pressure at reaction temperature. The reaction was effected for 170 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 28.9% and 37.6%, respectively.

EXAMPLE 25

0.5g of the catalyst of Example 13, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 115 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 26.6% and 45.7%, respectively.

EXAMPLE 26

0.5g of the catalyst of Example 14, and then 50g of a 20 weight percent solution of maleic acid in water, were placed in the glass liner of a 300 ml autoclave, which was then sealed, purged several times with hydrogen and then pressurized with hydrogen to 1100 psig. The autoclave was heated to 170° C. and the pressure adjusted to 1850 psig. As the reaction proceeded, additional hydrogen was added when the pressure dropped 50 to 100 psi to bring the pressure back to or near the original pressure at reaction temperature. The reaction was effected for 115 minutes, the reactor and contents cooled to room temperature, and the gas volume measured. The gases were analyzed by gas chromatography. The liquid phase was also analyzed by gas chromatography after filtering out the solids. The conversion of maleic acid was 100 percent, and the yields of γ-butyrolactone and 1,4-butanediol were 50.0% and 19.0%, respectively.

As will be evident to those skilled in the art various modifications of this invention can be made or followed in the light of the foregoing disclosure and discussion without departing from the spirit and scope of the disclosure or from the scope of the claims.

We claim:

1. A process for making one or both of γ-butyrolactone and 1,4-butanediol by the hydrogenation of maleic acid in the presence of a solid iron-containing ruthenium catalyst containing the elements and the ratios indicated by the empirical formula, $$RuFe_aM_bO_x$$

where
  M is one or more of Pd and Rh,
  a is 0.1–5,
  b is zero –3, and
  x is a number sufficient to satisfy the valency requirements of the cations present in the catalyst,
said catalyst having an atomic ratio of the sum of Zn+Cd to Ru no greater than 0.0001, said process being affected by contacting in a reaction zone an excess of hydrogen with an aqueous solution of maleic acid in admixture with said catalyst, wherein the weight ratio of water to maleic acid is at least 2:3.

2. A process according to claim 1 wherein the pressure in the reaction zone is not over 170 atmospheres.

3. A process according to claim 2 wherein the reaction temperature is in the range from 120–300° C.

4. A process according to claim 1 wherein the pressure in the reaction zone is not over 2100 psi gage.

5. A process according to claim 3 wherein the pressure in the reaction zone is not over 2100 psi gage.

* * * * *